US008993645B2

(12) United States Patent
Matsuno et al.

(10) Patent No.: US 8,993,645 B2
(45) Date of Patent: Mar. 31, 2015

(54) COMPOUND CONTAINING IMIDO GROUP, SOLUTION OF COMPOUND CONTAINING IMIDO GROUP AND METHOD FOR PRODUCING OF COMPOUND CONTAINING IMIDO GROUP

(71) Applicant: Nakata Coating Co., Ltd., Yokohama-shi, Kanagawa (JP)

(72) Inventors: Takemi Matsuno, Yokohama (JP); Katsuji Kitagawa, Yokohama (JP); Misao Hanazono, Yokohama (JP)

(73) Assignee: Nakata Coating Co., Ltd., Kanagawa (JP)

( * ) Notice: Subject to any disclaimer, the term of this patent is extended or adjusted under 35 U.S.C. 154(b) by 77 days.

(21) Appl. No.: 13/694,102

(22) Filed: Oct. 31, 2012

(65) Prior Publication Data
US 2013/0327253 A1    Dec. 12, 2013

(30) Foreign Application Priority Data

Jun. 12, 2012    (JP) .................. 2012-132468

(51) Int. Cl.
*C08J 11/04*    (2006.01)
*C07C 227/18*    (2006.01)
(Continued)

(52) U.S. Cl.
CPC ............. *C07C 227/18* (2013.01); *C08J 11/14* (2013.01); *C08J 11/16* (2013.01); *C08J 11/18* (2013.01); *C08J 2379/08* (2013.01); *C08L 79/08* (2013.01)
USPC ................ 521/49.8; 524/40; 428/402; 564/1; 106/287.25; 528/310; 528/491

(58) Field of Classification Search
CPC ......... C07C 227/18; C08J 11/14; C08J 11/16; C08J 11/18; C08J 2379/08; C09D 179/08; C08G 73/10; C08L 79/08
USPC .............. 521/40, 40.5, 48, 49, 49.8; 528/310, 528/491; 564/1; 106/287.25; 428/402
See application file for complete search history.

(56) References Cited

U.S. PATENT DOCUMENTS 3,952,084 A * 4/1976 Edelman et al. ........... 427/388.1
5,104,970 A    4/1992 Baron et al.
(Continued)

FOREIGN PATENT DOCUMENTS

EP    0 182 589    5/1986
JP    60-81154    5/1985
(Continued)

OTHER PUBLICATIONS

Extended European Search Report dated Oct. 8, 2013, including the European Search Report and the European Search Opinion, for EP Application No. 12007009.9-1303.
(Continued)

*Primary Examiner* — Frances Tischler
(74) *Attorney, Agent, or Firm* — Antonelli, Terry, Stout & Kraus, LLP.

(57) ABSTRACT

Provided by the invention is a compound containing an imido group that is obtained by partial hydrolysis of a polyimide molded article, in which the compound has an absorption peak derived from an imido group at wave number of 1375 $cm^{-1}$, an absorption peak derived from an amide group at wave number of 1600 $cm^{-1}$, and an absorption peak derived from a carboxyl group at wave number of 1413 $cm^{-1}$ in the IR spectrum chart obtained by IR spectroscopic measurement.

8 Claims, 8 Drawing Sheets

(51) Int. Cl.
  *C08J 11/14* (2006.01)
  *C08J 11/16* (2006.01)
  *C08J 11/18* (2006.01)
  *C08L 79/08* (2006.01)

(56) References Cited

U.S. PATENT DOCUMENTS

| | | |
|---|---|---|
| 5,604,041 A | 2/1997 | Choi |
| 5,756,650 A | 5/1998 | Kawamonzen et al. |
| 2009/0184347 A1 | 7/2009 | Maeda et al. |
| 2013/0289204 A1 | 10/2013 | Kanazawa |

FOREIGN PATENT DOCUMENTS

| | | |
|---|---|---|
| JP | 61-130369 | 6/1986 |
| JP | 06-157753 | 6/1994 |
| JP | 09-012883 | 1/1997 |
| JP | 2002-256104 | 9/2002 |
| JP | 2004-051672 | 2/2004 |
| JP | 2004-15813 | 4/2004 |
| JP | 2006-124530 | 5/2006 |
| JP | 2009-4394 | 1/2009 |
| JP | 2009-051957 | 3/2009 |
| JP | 4432175 | 1/2010 |
| JP | 2011-162570 | 8/2011 |
| JP | 2013-082876 | 5/2013 |
| WO | WO 95/10797 | 4/1995 |
| WO | WO 2012/096374 | 7/2012 |

OTHER PUBLICATIONS

Y. Zhai, et al., "The study of imidization degree of polyamic acid in solution and ordering degree of its polyimide film", *J. Matter Sci.* vol. 43, 2008, pp. 338-344.

T. Verdianz, et al., "Surface modification of imide containing polymer I: Catalytic groups" *European Polymer Journal*, vol. 42, 2006, pp. 638-654.

\* cited by examiner (a)

(b)

(c)

NON-COATED SURFACE (Al)

COATED SURFACE

COMPOUND CONTAINING IMIDO GROUP, SOLUTION OF COMPOUND CONTAINING IMIDO GROUP AND METHOD FOR PRODUCING OF COMPOUND CONTAINING IMIDO GROUP

BACKGROUND OF THE INVENTION

1. Field of the Invention

The present invention relates to a compound containing an imido group, a solution of the compound containing an imido group, and a method for producing of the compound containing an imido group.

In particular, it relates to a compound containing an imido group having a good low temperature curability, a good solubility, a good adhesion to a substrate, and the like in which the compound is obtained by partial hydrolysis of a polyimide molded article as industrial waste, a solution of the compound containing an imido group, and a method for producing of the compound containing an imido group.

2. Description of Related Art

Since a polyimide molded article represented by a polyimide film has an excellent chemical resistance, it is insoluble in various solvents and has high boiling point. As such thermoplastic plastics such as polystyrene, recycling after melting is conventionally difficult to achieve.

For such reasons, when a polyimide molded article needs to be discarded as waste, it is generally buried in the ground or incinerated in spite of high cost. Thus, a problem remains in that it is unsatisfactory in terms of a recycling property or environmental characteristics.

Under these circumstances, various methods have been suggested to chemically hydrolyze and recycle a polyimide molded article to be discarded.

For example, a method including complete hydrolysis of an aromatic polyimide molded article under a pre-determined temperature condition in the presence of alkali at a pre-determined concentration to give aromatic tetracarboxylic acid dianhydride and aromatic diamine as raw materials is known (see, the patent document 1).

More specifically, it is a method of treating polyimide which includes that the polyimide is hydrolyzed at 150 to 230° C. in the presence of 4 to 4.8 times the amount of alkali relative to the polyimide unit to give aromatic tetracarboxylic acid dianhydride and aromatic diamine as raw materials, an aqueous alkaline solution and an acidic solution of them are treated with activated charcoal, a large amount of acid and alkali are added to the mixture, and the aromatic tetracarboxylic acid dianhydride and aromatic diamine are precipitated, separated, and recovered.

Further, a method of hydrolyzing polyimide with a pre-determined structure under high temperature and high pressure condition in the presence of water or alcohol and obtaining it as a low molecular weight product, which is a raw material for polyimide, is suggested (see, the patent document 2).

More specifically, it is a method of dissociating polyimide including hydrolyzing polyimide or a polyamide acid as a precursor thereof under a supercritical condition including, for example, 250 to 350° C. and 10 to 100 MPa in the presence of water or alcohol and obtaining it as a low molecular weight product of aromatic tetracarboxylic acid dianhydride or aromatic diamine, which is a raw material for polyimide.

Further, a method of dissociating polyimide or the like from a polymer-containing solid which contains a metal compound and polyimide and recovering the metal component is suggested (see, the patent document 3).

More specifically, it is a method of contacting, at the temperature of 200° C. or higher, a polymer-containing solid such as polyimide with a polymer-dissociating material containing a solvent which has solubility parameter of 18 $(MJ/m^3)^{1/2}$ or more to dissociate and remove the polymer-containing solid and efficiently recovering the remaining metal component (copper).

Still further, a method of hydrolyzing polyimide as industrial waste by using a large amount of a basic material under low temperature and atmospheric pressure and recovering a pre-determined raw material for polyimide as a recycling material is suggested (see, the patent document 4).

More specifically, it is a method including adding a basic material (e.g., alkali metal hydroxide) capable of producing a hydroxide ion (OH) 20 to 80 molar times the theoretical dissociation amount to the polyimide, hydrolyzing the mixture under atmospheric pressure at a pre-determined temperature (40 to 95° C.), neutralizing the product with an acidic material, and recovering a raw material for polyamide such as pyromellitic acid or aromatic amine.

PRIOR ARTS

Patent Documents

[Patent Document 1] JPS60-81154A (Claims)
[Patent Document 2] JP4432175B (Claims)
[Patent Document 3] JP2002-256104A (Claims)
[Patent Document 4] JP2006-124530A (Claims)

SUMMARY OF THE INVENTION

However, the methods or the like for regenerating the polyimide molded article that are disclosed in the patent documents 1 to 4 basically have a purpose of obtaining a raw material for polyimide or remaining metal materials based on complete hydrolysis.

Thus, there is clearly no intention to obtain a compound containing an imido group with a specific structure which can be cured at low temperature and exhibits a good solubility or a good adhesion based on partial hydrolysis of a polyimide molded article.

More specifically, as the patent document 1 discloses a method of treating polyimide including precipitating aromatic tetracarboxylic acid dianhydride and aromatic diamine, and isolating and recovering it, obtainment of a compound containing an imido group with a specific structure is not suggested at all.

Further, as the patent document 2 discloses a treating method of polyimide to obtain aromatic tetracarboxylic acid dianhydride and aromatic diamine as a raw material for polyimide based on hydrolysis at supercritical condition including pre-determined temperature and pre-determined pressure, obtainment of a compound containing an imido group with a specific structure is not suggested at all.

Further, as the patent document 3 discloses a method of treating polyimide including dissociating and removing a polymer solid such as polyimide and recovering efficiently the remaining metal components, obtainment of a compound containing an imido group with a specific structure is not suggested at all.

Further, as the patent document 4 discloses a treating method of polyimide for recovering a raw material for polyimide such as pyromellitic acid and aromatic amine, obtainment of a compound containing an imido group with a certain a structure is not suggested at all.

Still further, according to the methods or the like for regenerating a polyimide molded article that are disclosed in the patent documents 1 to 4, no suggestion has been made regarding further lowering of curing temperature to regenerate polyimide from hydrolysates by containing a pre-determined reaction promoting agent (specific metal species).

In this regard, as a result of extensive studies, the inventors of the present invention have found that the aforementioned problems could be solved by partial hydrolysis of a polyimide molded article as industrial waste and by having a compound containing an imido group with a specific structure which has a pre-determined absorption peak in an infrared (IR) spectrum chart when measured by IR spectroscopy, and thus completed the invention accordingly.

That is, objects of the present invention are to provide a compound containing an imido group having a specific structure, which could be curable at low temperature, and has an excellent solubility and a good adhesion; a compound solution containing an imido group prepared by dissolving the compound containing an imido group in an organic solvent; and an efficient method for preparing the compound containing an imido group having the specific structure.

In order to solve the above problems, the present invention provides a compound containing an imido group obtained by partial hydrolysis of a polyimide molded article, wherein the compound has an absorption peak derived from an imido group at wave number of 1375 $cm^{-1}$ (including around the wave number of 1375 $cm^{-1}$ which is the same in the following description), an absorption peak derived from an amide group at wave number of 1600 $cm^{-1}$ (including around the wave number 1600 $cm^{-1}$ which is the same in the following description), and an absorption peak derived from a carboxyl group at wave number of 1413 $cm^{-1}$ (including around the wave number 1413 $cm^{-1}$ which is the same in the following description) in the IR spectrum chart obtained by IR spectroscopic measurement.

Specifically, by having a specific structure (functional group) in a partial hydrolysate of a polyimide molded article, a compound containing an imido group which could be cured at low temperature, has an excellent solubility for various solvents and an excellent adhesion to various substrates could be provided.

It is also found that the compound containing an imido group allows thermal polymerization for a pre-determined polyimide resin by thermal curing under a pre-determined condition, and the production cost is $\frac{1}{10}$ or less compared to the cost of conventional polyimide resin and a polyimide resin with equivalent heat resistance could be obtained. Thus, it can be said that use of the compound containing an imido group as a raw material for polyimide resin is quite advantageous from an economic point of view.

In addition, whether a polyimide molded article is partially hydrolyzed can be determined by the presence of an absorption peak derived from the imido group explained above, an absorption peak derived from an amide group, and an absorption peak derived from a carboxyl group in an IR spectrum chart.

Further, in order to constitute the compound containing an imido group according to the present invention, it is preferable that, in the IR spectrum chart, when the height of absorption peak at wave number of 1500 $cm^{-1}$, which is derived from a benzene ring, is S1 and the height of absorption peak at wave number of 1375 $cm^{-1}$, which is derived from an imido group, is S2, the ratio of S1/S2 is set to be a value within the range of 2 to 10.

According to the above constitution, not only the compound containing an imido group curable at low temperature could be obtained, but also it could be employed as an indicator whether a polyimide molded article is partially hydrolyzed.

Further, depending on the type of polyimide which constitutes the polyimide molded article, that is, type of the compound containing an imido group that is obtained by partial hydrolysis, the absorption peak (standard peak) at wave number of 1500 $cm^{-1}$, which is derived from a benzene ring, may not appear. Thus, in such case, it is possible to have other absorption peaks as a reference peak instead of the absorption peak at wave number of 1500 $cm^{-1}$ derived from a benzene ring.

Further, in order to constitute the compound containing an imido group according to the present invention, it is preferable that, in the IR spectrum chart, when the height of absorption peak at wave number of 1500 $cm^{-1}$, which is derived from a benzene ring, is S1 and the height of absorption peak at wave number of 1600 $cm^{-1}$, which is derived from an amide group, is S3, the ratio of S1/S3 is set to be a value within the range of 2 to 20.

According to the above constitution, not only the compound containing an imido group having more excellent solubility for a pre-determined organic solvent and a good adhesion property to various substrates could be obtained but also it could be employed as an indicator whether a polyimide molded article is partially hydrolyzed.

Further, in order to constitute the compound containing an imido group according to the present invention, it is preferable that, in the IR spectrum chart, when the height of absorption peak at wave number of 1500 $cm^{-1}$, which is derived from a benzene ring, is S1 and the height of absorption peak at wave number of 1413 $cm^{-1}$, which is derived from a carboxyl group, is S4, the ratio of S1/S4 is set to be a value within the range of 8 to 30.

According to the above constitution, not only the compound containing an imido group having more excellent solubility for a pre-determined organic solvent and a good adhesion property to various substrates could be obtained, but also it could be employed as an indicator whether a polyimide molded article is partially hydrolyzed.

Further, in order to constitute the compound containing an imido group according to the present invention, it is preferable that the compound includes a reaction promoting agent for promoting imidization reaction and content of the reaction promoting agent is set to be a value within the range of 0.05 to 5% by weight per total amount of the compound containing an imido group.

According to the above constitution, the compound containing an imido group curable at even lower temperature and having an excellent adhesion could be obtained.

Further, in order to constitute the compound containing an imido group according to the present invention, it is preferable that the compound containing an imido group has a particulate shape and the average particle diameter of the compound containing an imido group with the particulate shape is set to be a value within the range of 0.1 to 500 μm.

According to the above constitution, not only the compound containing an imido group which has better handling ability but also the compound containing an imido group which has more excellent solubility for a pre-determined organic solvent could be obtained.

Further, according to another aspect of the present invention, a solution of the compound containing an imido group includes a compound containing an imido group that is obtained by partial hydrolysis of a polyimide molded article and an organic solvent, wherein the compound containing an imido group has an absorption peak derived from an imido group at wave number of 1375 cm$^{-1}$, an absorption peak derived from an amide group at wave number of 1600 cm$^{-1}$, and an absorption peak derived from a carboxyl group at wave number of 1413 cm$^{-1}$ in the IR spectrum chart obtained by IR spectroscopic measurement.

According to the above constitution, not only the handling ability (workability) is improved but also a coating composition or the like which can be cured at low temperature and has an excellent liquid stability could be easily obtained.

Further, with respect to the solution of the compound containing an imido group, the compound containing an imido group may be completely dissolved in an organic solvent and present in a liquid state with high transparency, or the compound containing an imido group may be included in a partially swollen state in the solution of the compound containing an imido group.

Further, according to still another aspect of the present invention, a method for producing of a compound containing an imido group by partial hydrolysis of a polyimide molded article, includes the following steps (1) to (3) is provided.
(1) chopping the polyimide molded article to prepare it with a predetermined size,
(2) hydrolyzing the polyimide molded article with the predetermined size under the temperature condition of 50 to 100° C. in the presence of water and a basic compound to give a crude compound containing an imido group, and
(3) purifying the crude compound containing an imido group to give a compound containing an imido group which has an absorption peak derived from an imido group at wave number of 1375 cm$^{-1}$, an absorption peak derived from an amide group at wave number of 1600 cm$^{-1}$, and an absorption peak derived from a carboxyl group at wave number of 1413 cm$^{-1}$ in the IR spectrum chart obtained by IR spectroscopic measurement.

Specifically, according to partial hydrolysis of the polyimide molded article, a compound containing an imido group which could be cured at low temperature and has an excellent solubility for various organic solvents could be efficiently obtained.

Further, according to the method for producing of a compound containing an imido group according to the present invention, since the polyimide molded article is used as industrial waste, a pre-determined compound containing an imido group could be produced at very low cost. Accordingly, a polyimide resin having an excellent thermal resistance or the like could be obtained by thermal curing at low cost which is 1/10 or less than of the conventional cost, and therefore, it could be said that it is quite advantageous from an economic point of view compared to conventional methods for producing of a polyimide resin.

DETAILED DESCRIPTION OF EMBODIMENTS

[First Embodiment]

Figure 1:
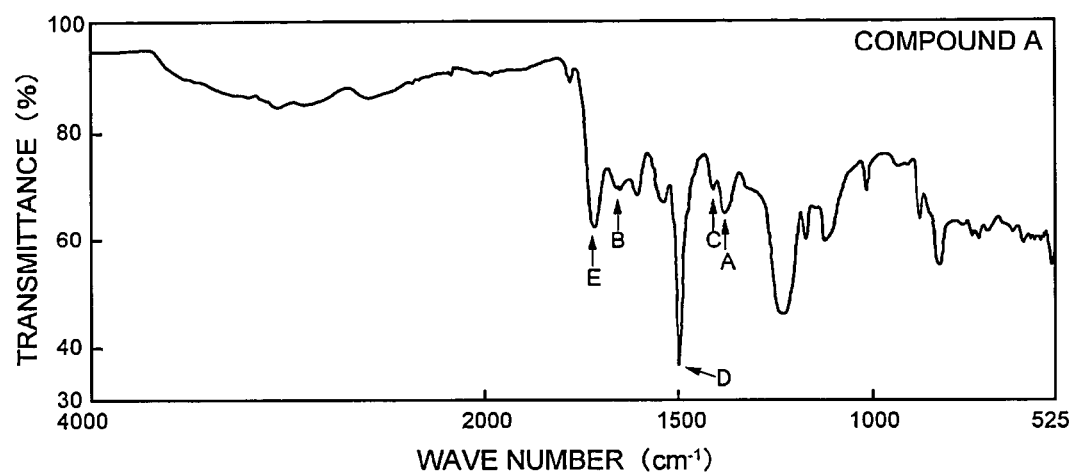
FIG. 1 is an IR spectrum chart of the compound containing an imido group (Compound A) according to the invention (Example 1)

The first embodiment relates to a compound containing an imido group that is obtained by partial hydrolysis of a polyimide molded article, as shown in the IR spectrum chart of FIG. 1, and it is a compound containing an imido group having an absorption peak (peak A) derived from an imido group at wave number of 1375 cm$^{-1}$, an absorption peak (peak B) derived from an amide group at wave number of 1600 cm$^{-1}$, and an absorption peak (peak C) derived from a carboxyl group at wave number of 1413 cm$^{-1}$ in the IR spectrum chart obtained by IR spectroscopic measurement.

Further, since the compound containing an imido group has an absorption peak (peak D) derived from the carbons of a benzene ring at wave number of 1500 cm$^{-1}$ and absorption peak (peak E) derived from a carbonyl group at wave number of 1710 cm$^{-1}$ in the IR spectrum chart, they could be used as a standard peak for carrying out qualitative analysis (characterization) of a compound.

1. Polyimide Molded Article

For producing a compound containing an imido group by partial hydrolysis, a polyimide molded article that has been conventionally treated as industrial waste or the like is widely targeted as a raw material.

Thus, preferred examples of the polyimide molded article include a polyimide film, a polyimide coating composition, polyimide resist, an electric part casing made of polyimide, a polyimide material for electronic part, a polyimide container, a polyimide mechanical part, a polyimide automotive part, and the like.

Further, even a circuit board in which a metallic circuit pattern is formed on the surface of a polyimide film or a composite laminate like TAB tape could be used as a polyimide molded article, which is a raw material for producing the compound containing an imido group according to the invention.

2. Partial Hydrolysate

Further, the compound containing an imido group according to the invention is, as shown in the IR spectrum chart of FIG. 1, a partial hydrolysate of the polyimide molded article having a pre-determined structure.

Specifically, as an example, it is a compound containing an imido group which is obtained by partial hydrolysis of a polyimide molded article with a pre-determined size under temperature condition of 50 to 100° C. in the presence of water and a basic compound, and the compound containing an imido group having a pre-determined structure represented by the formula (1) below is the subject.

As having at least an imido group, an amide group, and a carboxyl group, and also a carbonyl group or the like in a molecule consisting of carbon atoms and the like, a compound containing an imido group which can be cured at low temperature and has an excellent solubility for various organic solvents and an excellent adhesion property can be provided.

Formula (1)

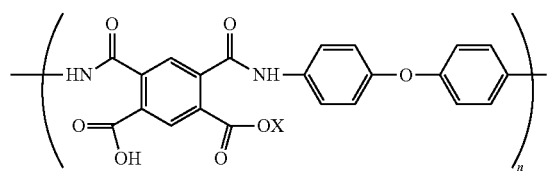

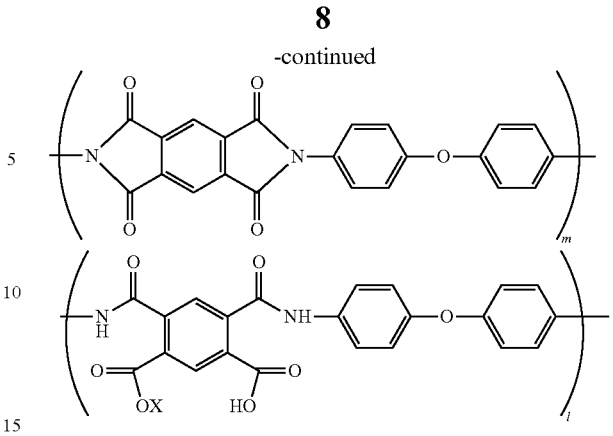

(in the formula (1), the symbol X represents an alkali metal (lithium/Li, sodium/Na, potassium/K, rubidium/Rb, or cesium/Ce), the subscripts n and l are the symbols representing the amount (molar number) of polyamide acid structure present at both sides of a polyimide structure, which have the value usually within the range of from 0.1 to 0.8, and the subscript m is the symbol representing the amount (molar number) of polyimide structure, which has the value usually within the range of from 0.2 to 0.9).

Further, it is estimated that the molecular terminal of the compound containing an imido group has a pre-determined structure that is represented by the following formula (2).

Specifically, it is estimated that the terminal structure of the molecule consists of, either singly or in combination, a polyamide acid structure represented by the symbol A, a mixture of a polyamide acid and an alkaline soap structure represented by the symbol B, and an alkaline soap structure represented by the symbol C.

Thus, by having such molecular terminal, a compound containing an imido group which can be cured at even lower temperature and has an excellent solubility for various organic solvents and an excellent adhesion property can be provided.

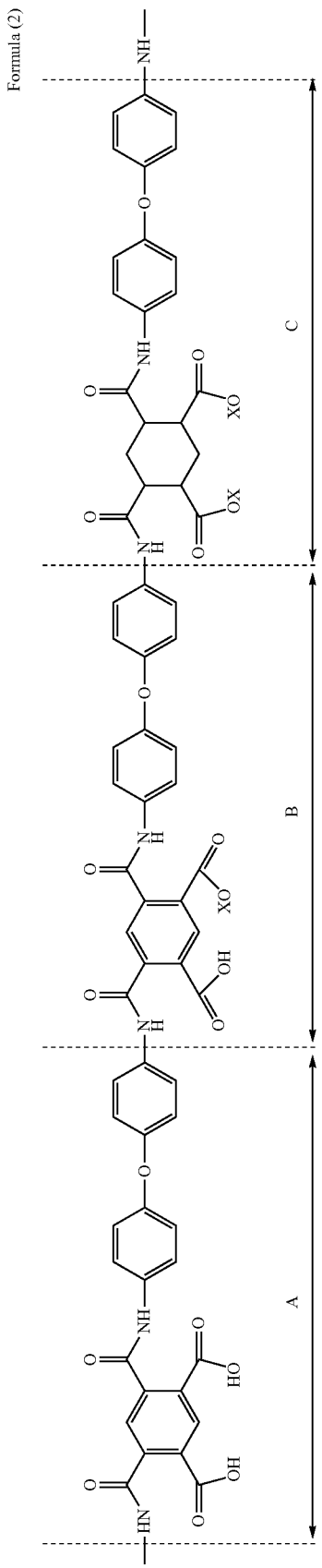

Meanwhile, it is not necessary for the compound containing an imido group to contain simultaneously an imido group, an amide group, and a carboxyl group in one molecule consisting of carbon atoms. Instead, it may be a mixture of polyimide having an imido group represented by the following formula (3)-1, polyamide acid having an amide group represented by the following formula (3)-2, and a carboxylic acid compound having a carboxyl group represented by the following formula (3)-3.

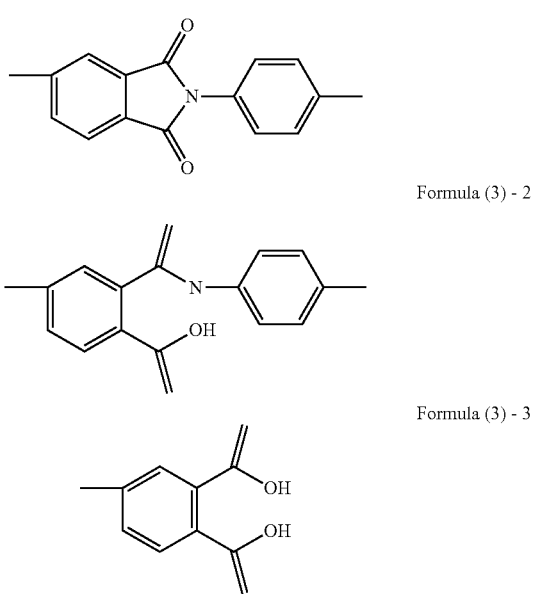

Formula (3) - 1

Formula (3) - 2

Formula (3) - 3

3. IR Spectrum Chart
(1) Imido Group

The compound containing an imido group according to the invention is characterized in that, as illustrated in the IR spectrum chart of FIG. 1 obtained by IR spectroscopic measurement, it has an absorption peak derived from an imido group at or near wave number of 1375 cm$^{-1}$.

The reason is that, by having an imido group in the molecule, a compound containing an imido group which can be cured at lower temperature can be provided, and also predetermined heat resistance can be exhibited when it is prepared as a polyimide resin according to polymerization by thermal curing treatment.

Figure 2:
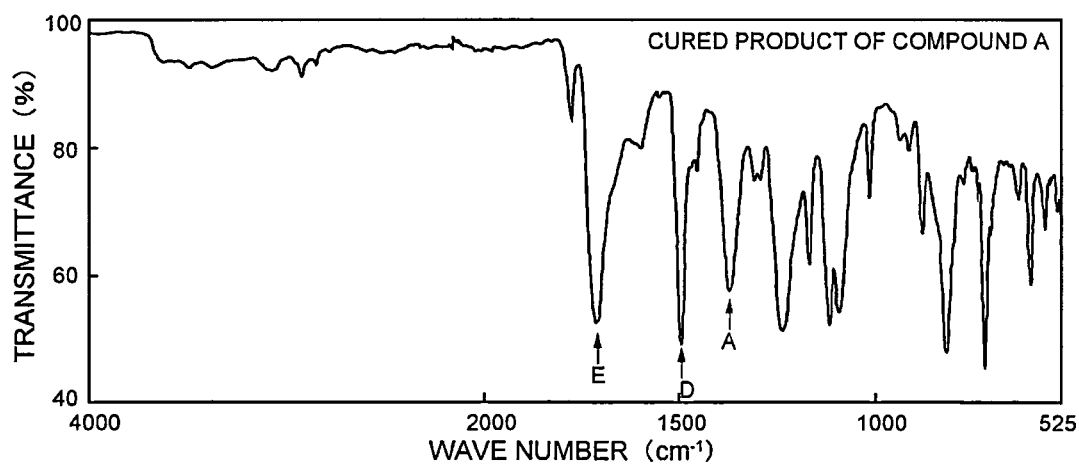
FIG. 2 is an IR spectrum chart of the cured product (polyimide resin) of the compound containing an imido group (Compound A) according to the invention (Example 1)

Further, as illustrated in the IR spectrum chart of FIG. 1, although it is possible that the amount of an imido group (peak height) of the compound containing an imido group according to the invention may be taken as an indicator for illustrating the degree of partial hydrolysis, when the amount of an imido group (peak height) in the IR spectrum chart of polyimide illustrated in FIG. 2 or the like is 100, it is preferably set to be a value within the range of 10 to 50. It is also found that it is more preferably in the range of 15 to 45, and still more preferably in the range of 20 to 40.

(2) Amide Group

The compound containing an imido group according to the invention is characterized in that, as illustrated in FIG. 1, it has an absorption peak derived from an amide group at or near wave number of 1600 cm$^{-1}$.

The reason is that, by having an amide group in the molecule, a compound containing an imido group which can be cured at even lower temperature can be provided.

It was also found that the compound containing an imido group according to the invention exhibits an absorption peak clearly derived from an amide group (waver number: 1600 cm$^{-1}$) as illustrated in the IR spectrum chart of FIG. 1 but the polyimide obtained by curing has no such absorption peak derived from an amide group as illustrated in FIG. 2 or the like.

(3) Carboxyl Group

The compound containing an imido group according to the invention is also characterized in that, as illustrated in FIG. 1, it has an absorption peak derived from a carboxyl group at or near wave number of 1413 cm$^{-1}$.

The reason is that, by having a carboxyl group in the molecule, a compound containing an imido group having good solubility or adhesion property can be provided.

It was also found that the compound containing an imido group according to the invention exhibits an absorption peak derived from a carboxyl group (wave number: 1413 cm$^{-1}$) as illustrated in the IR spectrum chart of FIG. 1 but the polyimide obtained by thermal curing has no such absorption peak derived from a carboxyl group as illustrated in FIG. 2 or the like.

(4) Carbonyl Group

The compound containing an imido group according to the invention is characterized in that, as illustrated in FIG. 1, it preferably has an absorption peak derived from a carbonyl group at or near wave number of 1710 cm$^{-1}$.

The reason is that, by having a carbonyl group in the molecule, a compound containing an imido group having better solubility can be provided.

Further, as illustrated in the IR spectrum chart of FIG. 1, although it is possible that the amount of a carbonyl group (peak height) of the compound containing an imido group according to the invention may be taken as an indicator for illustrating the degree of partial hydrolysis, when the amount of a carbonyl group (peak height) in the IR spectrum chart of polyimide illustrated in FIG. 2 or the like is 100, it is preferably set to be a value within the range of 30 to 70. It is also found that it is more preferably in the range of 35 to 60, and still more preferably in the range of 40 to 50.

(5) Ratio Relative to Benzene Ring
(5)-1 S1/S2

Further, in the IR spectrum chart of the compound containing an imido group according to the invention, when the height of absorption peak at wave number of 1500 cm$^{-1}$, which is derived from a benzene ring, is S1 and the height of absorption peak at wave number of 1375 cm$^{-1}$, which is derived from an imido group, is S2, it is preferable that the ratio of S1/S2 is set to be a value within the range of 2 to 10.

The reason is that, by having the presence ratio of an imido group within the range described above, not only a compound containing an imido group which can be cured at even lower temperature can be provided but also it may be taken as an indicator for illustrating the degree of partial hydrolysis.

Accordingly, the S1/S2 ratio is more preferably set to be a value within the range of 3 to 8. The S1/S2 ratio is still more preferably set to be a value within the range of 5 to 7.

(5)-2 S1/S3

Further, in the IR spectrum chart of the compound containing an imido group according to the invention, when the height of absorption peak at wave number of 1500 cm$^{-1}$, which is derived from a benzene ring, is S1 and the height of absorption peak at wave number of 1600 cm$^{-1}$, which is derived from an amide group, is S3, it is preferable that the ratio of S1/S3 is set to be a value within the range of 2 to 20.

The reason is that, by having the presence ratio of an amide group within the range described above, not only a compound containing an imido group which has better solubility for a pre-determined organic solvent and better adhesion property can be provided but also it may be taken as an indicator for illustrating the degree of partial hydrolysis.

Accordingly, the S1/S3 ratio is more preferably set to be a value within the range of 5 to 15. The S1/S3 ratio is still more preferably set to be a value within the range of 7 to 12.

(5)-3 S1/S4

Further, in the IR spectrum chart of the compound containing an imido group according to the invention, when the height of absorption peak at wave number of 1500 cm$^{-1}$, which is derived from a benzene ring, is S1 and the height of absorption peak at wave number of 1413 cm$^{-1}$, which is derived from a carboxyl group, is S4, it is preferable that the ratio of S1/S4 is set to be a value within the range of 8 to 30.

The reason is that, by having the presence ratio of a carboxyl group within the range described above, not only a compound containing an imido group which has better solubility for a pre-determined organic solvent and better adhesion property can be provided but also it may be taken as an indicator for illustrating the degree of partial hydrolysis.

Accordingly, the S1/S4 ratio is more preferably set to be a value within the range of 10 to 25. The S1/S4 ratio is still more preferably set to be a value within the range of 13 to 20.

4. Weight Average Molecular Weight

The weight average molecular weight of the compound containing an imido group according to the invention is preferably set to be a value within the range of 1,000 to 100,000.

The reason is that, by having such weight average molecular weight, not only low temperature curability is exhibited but also good solubility for an organic solvent is obtained.

Accordingly, the weight average molecular weight of the compound containing an imido group is preferably set to be a value within the range of 3,000 to 60,000. More preferably, it is set to be a value within the range of 5,000 to 30,000.

Further, the weight average molecular weight of the compound containing an imido group can be measured by gel permeation chromatography using polystyrene as reference material.

5. Reaction Promoting Agent (1) Types

For constituting the compound containing an imido group according to the invention, it is preferable to include a reaction promoting agent for promoting an imidization reaction.

The reason is that, by including a reaction promoting agent in the compound containing an imido group, a compound containing an imido group which can be cured at even lower temperature can be provided.

As for the type of the reaction promoting agent, any compound capable of promoting imidization to yield a polyimide resin can be used. Preferably, it includes at least one metal element of potassium element, silicon element, calcium element, iron element, chrome element, and the like.

Further, it is also preferable that potassium hydroxide or calcium hydroxide is used for partial hydrolysis of a polyimide molded article and a pre-determined amount of potassium element or calcium element derived from potassium hydroxide or the like is maintained during purification of a compound containing an imido group for exhibition of the pre-determined effect of the reaction promoting agent.

(2) Content

Content of the reaction promoting agent is preferably set to be a value within the range of 0.05 to 5% by weight per total amount of the compound containing an imido group.

The reason is that, by limiting the content of the reaction promoting agent, a compound containing an imido group which can be cured at even lower temperature can be provided.

Accordingly, the content of the reaction promoting agent is more preferably set to be a value within the range of 0.1 to 2% by weight per total amount of the compound containing an imido group. Still more preferably, it is set to be a value within the range of 0.2 to 0.8% by weight.

6. Particulate Shape

For constituting the compound containing an imido group according to the invention, it is preferable that the compound containing an imido group has a particulate shape and the average particle diameter is set to be a value within the range of 0.1 to 500 μm.

The reason is that, by having such constitution, not only the handling ability of the compound containing an imido group is improved but also a compound containing an imido group which has more excellent solubility for a pre-determined organic solvent can be provided.

Accordingly, the average particle diameter of the compound containing an imido group is more preferably set to be a value within the range of 5 to 100 μm. Still more preferably, it is set to be a value within the range of 10 to 50 μm.

Further, the average particle diameter of the compound containing an imido group can be measured with reference to JIS Z8901.

7. Characteristics (1) Low Temperature Curability

Regarding the low temperature curability of the compound containing an imido group, it is preferable that the compound is thermally cured under condition with temperature of 200° C. or lower, more preferably 150° C. or lower, and still more preferably 120° C. or lower to yield pre-determined polyimide.

Accordingly, when the compound containing an imido group (Compound A) of the IR spectrum chart illustrated in FIG. 1 is treated under heating condition including 100° C. to 200° C. for 30 minutes, for example, the polyimide of the IR spectrum chart illustrated in FIG. 2 is preferably yielded (with imidization ratio of 70% or more).

More specifically, when the compound containing an imido group is thermally cured under heating condition including 100° C. to 150° C. for 30 minutes, a pre-determined polyimide film can be stably formed even with a substrate containing an olefin resin like polypropylene.

Further, with thermal curing under heating condition including the temperature higher than 150° C. to 200° C. for 30 minutes, a pre-determined polyimide film can be stably formed not only with a metal substrate or a ceramic substrate but also with a resin substrate containing a polyester resin or the like.

(2) Solubility

With respect to the solubility of the compound containing an imido group, it is preferable that the compound is sufficiently and also quickly dissolved in an organic solvent like N-methyl-2-pyrrolidone and N,N-dimethyl acetamide.

Specifically, when the compound containing an imido group (Compound A) of the IR spectrum chart illustrated in FIG. 1 is dissolved in N-methyl-2-pyrrolidone to have solid content concentration of 10 to 30% by weight, and preferably 12 to 20% by weight, by using a stirring apparatus like a homo mixer and a planetary mixer, it is preferable that a homogenous solution is obtained within 60 minutes. It is more preferable that a homogenous solution is obtained within 30 minutes by mixing procedure and the like.

8. Use

Use of the compound containing an imido group according to the invention is, although not specifically limited, a polyimide film, a polyimide coating composition, a polyimide electric insulating material, and the like which have a favorable heat resistance or the like after thermal curing at pre-determined temperature, and also various heat resistant polyimide molded articles like a heat resistant electric part casing, a heat resistant electronic part material, a heat resistant circuit board, a heat resistant container, a heat resistant mechanical part, and a heat resistant automotive part.

Herein, embodiments of the use of the compound containing an imido group are explained in more detail in view of FIGS. 3A to 3E.

Figure 3A:
FIGS. 3A to 3E are the drawings for explaining embodiments of the use of the compound containing an imido group.

Firstly, the representative use of the compound containing an imido group is, as illustrated in FIG. 3A, a monolayer polyimide film 10 for improving heat resistance, an electric insulating property, or the like, and it can be obtained by heating (thermal curing) of the compound containing an imido group according to the invention under pre-determined condition.

Figure 3B:
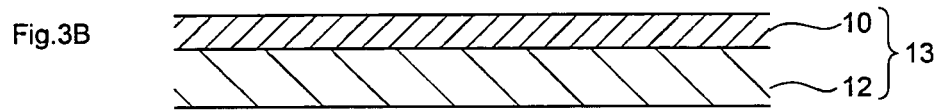

Further, as illustrated in FIG. 3B, a composite resin film 13 obtained by laminating the polyimide film 10 to improve heat resistance or an electric insulating property of another resin film 12 is also a preferable embodiment. Specifically, it is also a preferable embodiment that, on surface of the resin film 12 like a polyester film or a polyolefin film, the polyimide film 10 derived from the compound containing an imido group according to the invention is formed to have the configuration of the composite resin film 13 which has a good heat resistance or the like.

Figure 3C:
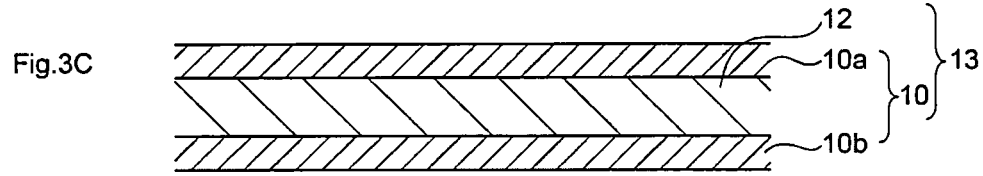

Further, as a modified example of the composite resin film 13 illustrated in FIG. 3B, the composite resin film 13' obtained by laminating the polyimide film 10 (10a and 10b) on both sides of the other resin film 12 is also a preferable embodiment as illustrated in FIG. 3C.

Figure 3D:
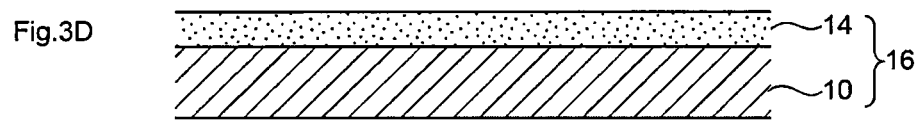

Further, as illustrated in FIG. 3D, it is also a preferable embodiment to have a configuration of the metal composite polyimide film 16 by forming the metal layer 14 on single surface of the polyimide film 10. According to the metal composite polyimide film 16, an adhesive layer between the polyimide film 10 and the metal layer 14 could be omitted, and therefore it may contribute to obtain the metal composite polyimide film 16 in a state of thin film.

Figure 3E:
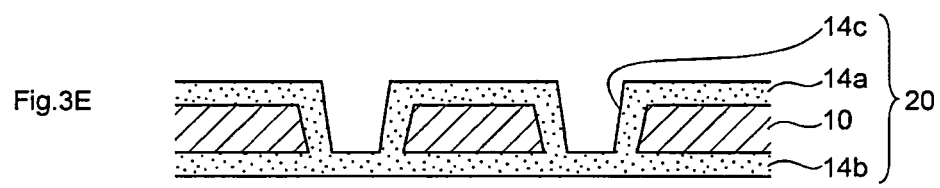

Further, as illustrated in FIG. 3E, it is also preferable to have the two-side circuit board 20 by forming the first metal layer 14a and the second metal layer 14b on both sides of the polyimide film 10 and forming the via hole 14c for electrically connecting the first metal layer 14a to the second metal layer 14b.

[Second Embodiment]

The second embodiment relates to a solution of the compound containing an imido group which includes a compound containing an imido group that is obtained by partial hydrolysis of a polyimide molded article, and an organic solvent, characterized in that the solution of the compound containing an imido group has an absorption peak derived from an imido group at wave number of 1375 cm$^{-1}$, an absorption peak derived from an amide group at wave number of 1600 cm$^{-1}$, and an absorption peak derived from a carboxyl group at wave number of 1413 cm$^{-1}$ in the IR spectrum chart obtained by IR spectroscopic measurement.

1. Compound Containing an Imido Group

The compound containing an imido group is the same as those explained for the first embodiment, and therefore no further explanations are given herein.

2. Organic solvent (1) Types

Types of the organic solvent for the solution of the compound containing an imido group are, although not specifically limited, preferably at least one of N-methyl-2-pyrrolidone, N,N-dimethyl formamide, N,N-dimethyl acetamide, methyl diglyme, methyl triglyme, dioxane, tetrahydrofuran, cyclohexanone, cyclopentanone, γ-butyrolactone, toluene, ethyl acetate, butyl acetate, cellosolve, methyl ethyl ketone, anisole, and the like.

In particular, N-methyl-2-pyrrolidone and N,N-dimethyl acetamide are a preferred organic solvent since the compound containing an imido group has an excellent solubility in those solvents so that it can be solubilized to quite high solid content concentration.

It is also preferable that the compound containing an imido group is fully solubilized in N-methyl-2-pyrrolidone or the like and a pre-determined amount of water, alcohol, or the like (for example, 1 to 30% by weight in the total amount of organic solvent) is further added to give an aqueous solution or an alcohol solution of the compound containing an imido group having a good uniform, highly stable properties, and the like.

(2) Content

The content of the organic solvent in a solution of the compound containing an imido group, in terms of solid content concentration, is preferably set to be a value within the range of 1 to 40% by weight.

With respect to the content of the organic solvent, by adjusting the content of the solid content concentration of the compound containing an imido group to a pre-determined range, not only the handling ability is improved, but also coating and drying properties could be easily performed and other addition components like a thermoplastic resin component, a thermosetting resin component, a photocurable resin component, a metal material, and a ceramic material could be uniformly and quickly added.

Thus, for adjusting the content of the solid content concentration in the compound containing an imido group, the content of the organic solvent is preferably set to be a value within the range of 5 to 30% by weight, and more preferably set to be a value within the range of 10 to 20% by weight per the total amount of the solution of the compound containing an imido group.

3. Viscosity

Viscosity of the solution of the compound containing an imido group is preferably adjusted to set be a value in the range of 100 to 500,000 mPa·sec (measurement temperature: 25° C., ditto in the followings).

The reason is that, by limiting the viscosity of the solution of the compound containing an imido group to a pre-determined range, not only the handling ability is improved but also coating and drying can be easily performed and other addition components like a thermoplastic resin component, a thermosetting resin component, a photocurable resin component, a metal material, and a ceramic material can be uniformly and quickly added.

Thus, viscosity of the solution of the compound containing an imido group is preferably set to be a value within the range of 1,000 to 100,000 mPa·sec, and more preferably set to be a value within the range of 5,000 to 50,000 mPa·sec.

3. Additives

Within the range that the characteristics of the solution of the compound containing an imido group are not impaired, various additives may be further added.

Specifically, it is preferable to add at least one of a fluoro resin, an epoxy resin, a phenol resin, a silicone resin, a urethane resin, an olefin resin (including an acryl resin), a polyester resin, a polyamide resin, a carbon resin, and the like.

Further, depending on the use of the polyimide or the like obtained after thermal curing, it is also preferable to add at least one of a colorant like dye and pigment, a conductive material, an electric insulating material, a UV absorbing agent, a radiation absorbing agent, a cross linking agent, a viscosity controlling agent, a matting agent, a light-weight material, fibers, and the like.

[Third Embodiment]

The third embodiment relates to a method for producing of the compound containing an imido group by partial hydrolysis of a polyimide molded article, the method including the following steps (1) to (3):
(1) chopping the polyimide molded article to prepare it with a pre-determined size,
(2) hydrolyzing the polyimide molded article with a pre-determined size under the temperature condition of 50 to 100° C. in the presence of water and a basic compound to give a crude compound containing an imido group, and
(3) purifying the crude compound containing an imido group to give a compound containing an imido group which has an absorption peak derived from an imido group at wave number of 1375 $cm^{-1}$, an absorption peak derived from an amide group at wave number of 1600 $cm^{-1}$, and an absorption peak derived from a carboxyl group at wave number of 1413 $cm^{-1}$ in the IR spectrum chart obtained by IR spectroscopic measurement.

1. Step (1)

Step (1) is a process of chopping a polyimide molded article so that it is prepared to have a pre-determined size.

The polyimide molded article as industrial waste is preferably chopped or subjected to size classification by using a chopping device, a grinding device, a sizing device, or the like so that the maximum width or average particle diameter is controlled in advance.

Thus, to achieve more uniform and quick partial hydrolysis, the polyimide molded article as industrial waste or the like is preferably chopped or subjected to size classification by using a cutter, a knife, a chopper, a shredder, a ball mill, a grinding device, a sieve, a punching metal, a cyclone, or the like so that the maximum width or average particle diameter is controlled in advance.

More specifically, when the polyimide molded article is prepared to have a rectangular shape, the average width is preferably 10 mm or less, and more preferably set to be a value within the range of 1 to 5 mm.

Further, when the polyimide molded article is prepared to have a particulate shape, the average particle diameter is preferably 10 mm or less, and more preferably set to be a value within the range of 1 to 5 mm.

Further, to have more maximum width or average particle diameter, it is preferable that the article is ground by supplying it to a resin grinder equipped with a punching metal, a sieve or the like while cooling it using dry ice or the like, and thus a ground polyimide product with small piece or particulate shape is obtained.

2. Step (2)

Step (2) is a process of partial hydrolysis of the polyimide molded article with a pre-determined size under temperature condition of 40 to 100° C., or preferably 50 to 80° C., in the presence of at least water and a basic compound so as to obtain a crude compound containing an imido group.

Thus, the polyimide molded article is preferably hydrolyzed under a pre-determined temperature condition, for example, for 1 to 48 hours under atmospheric pressure, in the presence of at least water and a basic compound.

As described herein, the basic compound means a compound for generating a hydroxide ion. Examples thereof include a hydroxide, a carbonate, a hydrogen carbonate, and also a fatty acid salt of an alkali metal or an alkali earth metal like sodium hydroxide, potassium hydroxide, calcium hydroxide, sodium hydrogen carbonate, potassium hydrogen carbonate, sodium acetate, potassium acetate, and sodium propionate, ammonia, ammonium carbonate, ammonium hydrogen carbonate, ammonium acetate, hydroxylamine, hydrazine, tetramethyl ammonium hydroxide, tetraethyl ammonium hydroxide, and an organic amine compound.

In particular, from the viewpoint that hydrolysis can occur at relatively low temperature and gently, sodium hydroxide or potassium hydroxide is preferably used.

Further, as described above, by confirming the presence or absence of an absorption peak derived from an imido group, an absorption peak derived from an amide group, or an absorption peak derived from a carboxyl group, and also confirming that height of each peak and relative height ratio or the like compared to the absorption peak derived from the benzene ring are within the pre-determined ranges in the IR spectrum chart obtained by IR spectroscopic measurement, whether the desired crude compound containing an imido group according to partial hydrolysis of a polyimide molded article is obtained can be determined.

3. Step (3)

Step (3) is a process of purifying the crude compound containing an imido group to obtain a compound containing an imido group which has an absorption peak derived from an imido group at wave number of 1375 $cm^{-1}$, an absorption peak derived from an amide group at wave number of 1600 $cm^{-1}$, and an absorption peak derived from a carboxyl group at wave number of 1413 $cm^{-1}$ in the IR spectrum chart obtained by IR spectroscopic measurement.

Thus, it is preferable that, by repeatedly performing 1 to 10 times a series of process including an acidic treatment (hydrochloric acid, nitric acid, sulfuric acid treatment, or the like), washing with water, an alkaline treatment (treatment with sodium hydroxide, potassium hydroxide, sodium carbonate, potassium carbonate, or the like), and washing with water, the crude compound containing an imido group is purified, and a compound containing an imido group with no impurities can be obtained.

Further, sufficient purification of the crude compound containing an imido group can be confirmed by determining that elements (or elemental ions) like chlorine, sulfur, phosphorus, aluminum, and magnesium which are the same or less than a pre-determined amount based on quantification by ion chromatography or X ray photoelectron spectroscopy (XPS).

More specifically, the purification degree of the crude compound containing an imido group can be determined by quantification with ion chromatography by confirming that the chloride ions are 100 ppm or less, more preferably 10 ppm or less, and still more preferably 1 ppm or less.

EXAMPLES

Herein below, the invention is explained in greater detail in view of the Examples.

Example 1

1. Preparation of Compound Containing an Imido Group (1) Step 1

As a polyimide molded article, Kapton film (trademark, mixture of Kapton-100H and other Kapton films in which Kapton-100H is a main component, manufactured by DU PONT-TORAY CO., LTD.) was chopped by using a chopper to have a rectangular shape with width of 10 mm or less.

Subsequently, while being cooled by addition of dry ice, it was supplied to a resin grinder equipped with a punching metal with diameter of 3 mm (Model No. P-1314, HORAI Co, Ltd.) to obtain the polyimide molded article (average particle diameter: about 3 mm) which has passed through the punching metal, as a ground polyimide product to be subjected to partial hydrolysis.

(2) Step 2

Subsequently, to a container (1000 mL) equipped with a stirrer, 5 g of thus-obtained ground polyimide product, 400 g of ion exchange water, and 2 g of potassium hydroxide as a basic material were added.

Subsequently, after heating the container temperature to 50° C., the solubilized product was subjected to hydrolysis for 24 hours under stirring to give a solution containing the crude compound containing an imido group.

(3) Step 3

Subsequently, for the solution containing the crude compound containing an imido group, by repeatedly performing 5 times a series of process including an acidic treatment, washing with water, an alkaline treatment, and washing with water, the crude compound containing an imido group was purified to give the particulate compound containing an imido group (average particle diameter: 30 μm).

In addition, it was confirmed by quantification analysis that, in the particulate compound containing an imido group, potassium is contained in an amount of about 0.2% by weight, Si is contained in an amount of about 0.02% by weight, Ca is contained in an amount of about 0.02% by weight, and Fe is contained in an amount of 0.005% by weight.

2. Evaluation of Compound Containing an Imido Group (1) FT-IR analysis (Evaluation 1)

The particulate compound containing an imido group obtained from above was dissolved in N-methyl-2-pyrrolidone (NMP) to have the solid content concentration of 15% by weight, and thus a film of the compound containing an imido group with thickness of 10 μm was prepared. By using IR spectrophotometer (FT-IR), presence of various functional groups (imido group, amide group, carboxyl group, carbonyl group, benzene ring, and the like) was determined based on ATR method.

Further, the IR spectrum chart of the compound containing an imido group obtained was illustrated in FIG. 1. The IR spectrum chart of the cured product of the compound containing an imido group (condition for thermal curing: 150° C. for 30 min), that is, the IR spectrum chart of polyimide, was illustrated in FIG. 2.

Figure 4:
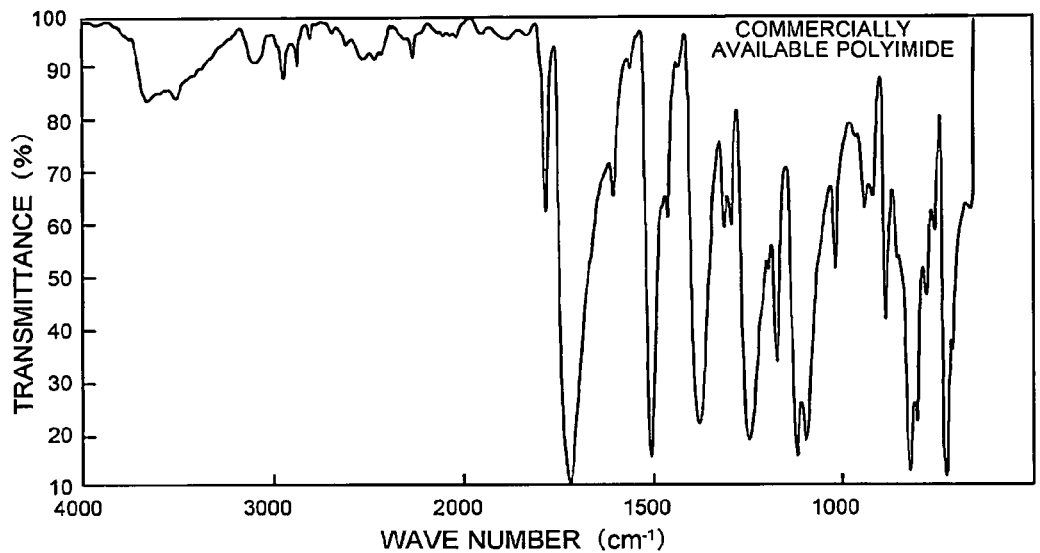
FIG. 4 is an IR spectrum chart of commercially available polyimide (Kapton H)

Further, as a reference, the IR spectrum chart of a commercially available polyimide (Kapton H) was illustrated in FIG. 4.

(2) Solubility (Evaluation 2)

By using a stirrer (homo mixer), the particulate compound containing an imido group obtained from above was dissolved in N-methyl-2-pyrrolidone to have the solid content concentration of 15% by weight. After that, the solubility of the compound containing an imido group was evaluated according to the following criteria.

Very Good The compound can be dissolved within 30 min.
Good: The compound can be dissolved within 60 min.
Fair: The compound can be dissolved within 120 min.
Bad: The compound cannot be dissolved even after 120 min.

(3) Low Temperature Curability (Evaluation 3)

The particulate compound containing an imido group obtained from above was dissolved in N-methyl-2-pyrrolidone to prepare a solution of the compound containing an imido group which has the solid content concentration of 15% by weight.

Thus-obtained solution of the compound containing an imido group was coated on a soft steel plate (length: 80 mm, width: 30 mm, and thickness: 1 mm) and thermally cured under each heating condition of 120° C. for 30 min and 150° C. for 30 min to form a polyimide film with thickness of 20 μm. After that, the low temperature curability was evaluated according to the following criteria.

Very good: By heating at both 120° C. and 150° C., a strong polyimide film can be formed.
Good: By heating at 120° C., the obtained polyimide film is slightly soft. However, by heating at 150° C., a strong polyimide film can be formed.
Fair: By heating at 120° C., the obtained polyimide film is soft.
However, by heating at 150° C., an almost strong polyimide film can be formed.
Bad: By heating both at 120° C. and 150° C., curing is insufficient and a strong polyimide film cannot be formed.

(4) Adhesion (Evaluation 4)

The polyimide film obtained above for evaluation of low temperature curability (the product obtained by curing at 150° C. for 30 min) was subjected to a cross-cut test in accordance with JIS K-5400. After that, the adhesion property was evaluated according to the following criteria.

Very good: Number of peeling off is 0/100 cross cut.
Good: Number of peeling off is 1 to 5/100 cross cut.
Fair: Number of peeling off is 6 to 10/100 cross cut.
Bad: Number of peeling of is at least 11/100 cross cut.

(5) Heat Resistance (Evaluation 5)

Figure 5:
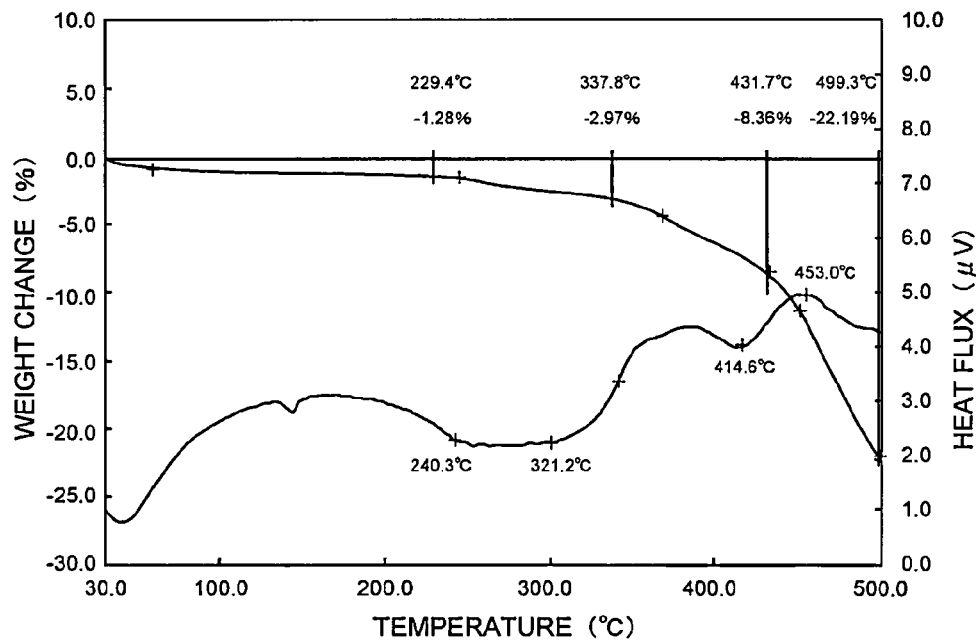
FIG. 5 is a thermogravimetry-differential thermal analysis (TG-DTA curve) chart of the cured product (polyimide resin) of the compound containing an imido group (Compound A) according to the invention (Example 1)

The polyimide film obtained above for evaluation of low temperature curability (the product obtained by curing at 150° C. for 30 min) was heated to 30 to 500° C. in nitrogen atmosphere by using differential thermal analyzer (TG-DTA) to measure heat resistance (temperature increase rate: 10° C./min). As a result, the differential thermal analyzer chart (TG-DTA curve) was obtained as illustrated in FIG. 5. Thereafter, based on the TG curve of the TG-DTA curve, the heat resistance of the polyimide film was evaluated according to the following criteria.

Very good: Temperature for 10% by weight decrease is 450° C. or higher.
Good: Temperature for 10% by weight decrease is 400° C. or higher.
Fair: Temperature for 10% by weight decrease is 350° C. or higher.
Bad: Temperature for 10% by weight decrease is lower than 350° C.

Example 2

In the Example 2, the solubility and the like of the compound containing an imido group were evaluated in the same manner as the Example 1 except that the type of the Kapton film as a polyimide molded article is changed to Kapton H (manufactured by DU PONT-TORAY CO., LTD.) and the hydrolysis time is changed to 36 hours to modify the degree of hydrolysis of the polyimide molded article, and thus a compound containing an imido group is obtained (Compound B).

Figure 6:
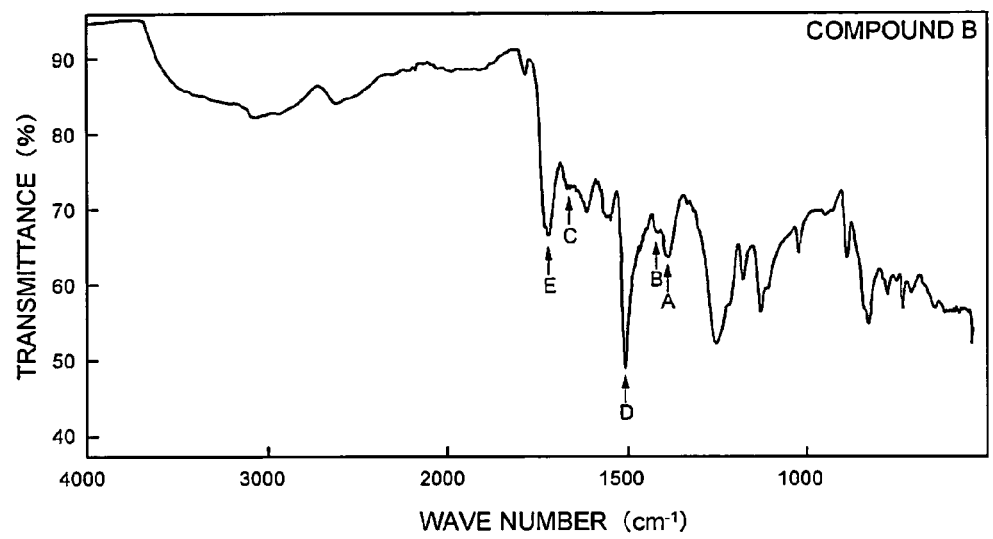
FIG. 6 is an IR spectrum chart of the compound containing an imido group (Compound B) according to the invention (Example 2)
Figure 7:
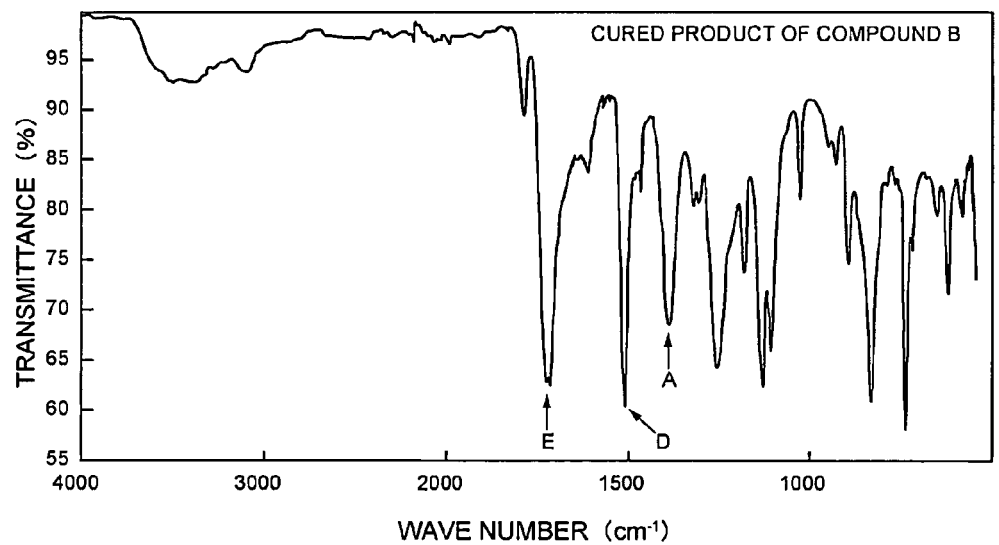
FIG. 7 is an IR spectrum chart of the thermally cured product (polyimide resin) of the compound containing an imido group (Compound B) according to the invention (Example 2)

Further, the IR spectrum chart of the compound containing an imido group obtained was illustrated in FIG. 6. The IR spectrum chart of the cured product of the compound containing an imido group (condition for thermal curing: 150° C. for 30 min), that is, the IR spectrum chart of polyimide, was illustrated in FIG. 7.

Example 3

In the Example 3, the solubility and the like of the compound containing an imido group were evaluated in the same manner as the Example 1 except that the type of the Kapton film as a polyimide molded article is changed to Kapton EN (trade name, manufactured by DU PONT-TORAY CO., LTD.) and the hydrolysis time is shortened to 12 hours to modify the degree of hydrolysis of the polyimide molded article, and thus a compound containing an imido group is obtained (Compound C).

Figure 8:
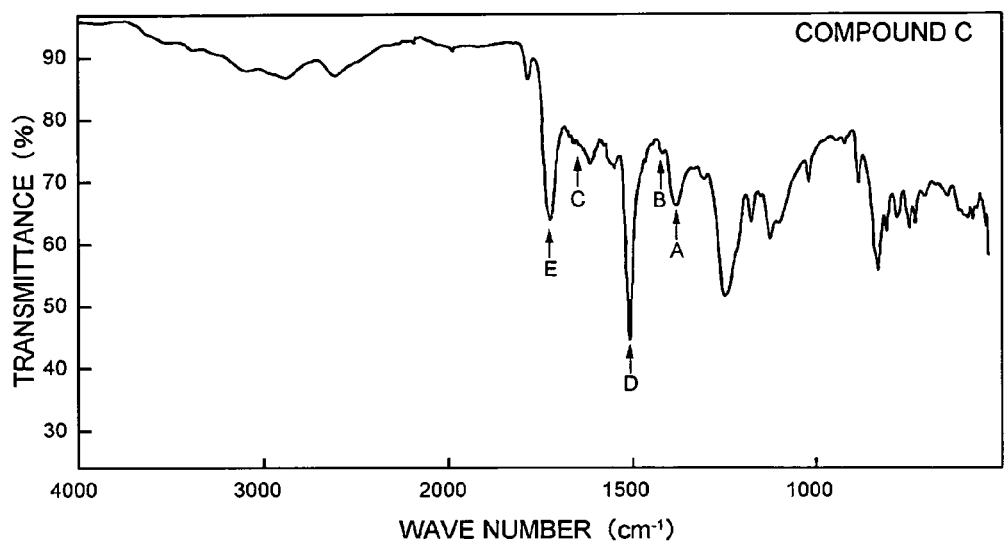
FIG. 8 is an IR spectrum chart of the compound containing an imido group (Compound C) according to the invention (Example 3)
Figure 9:
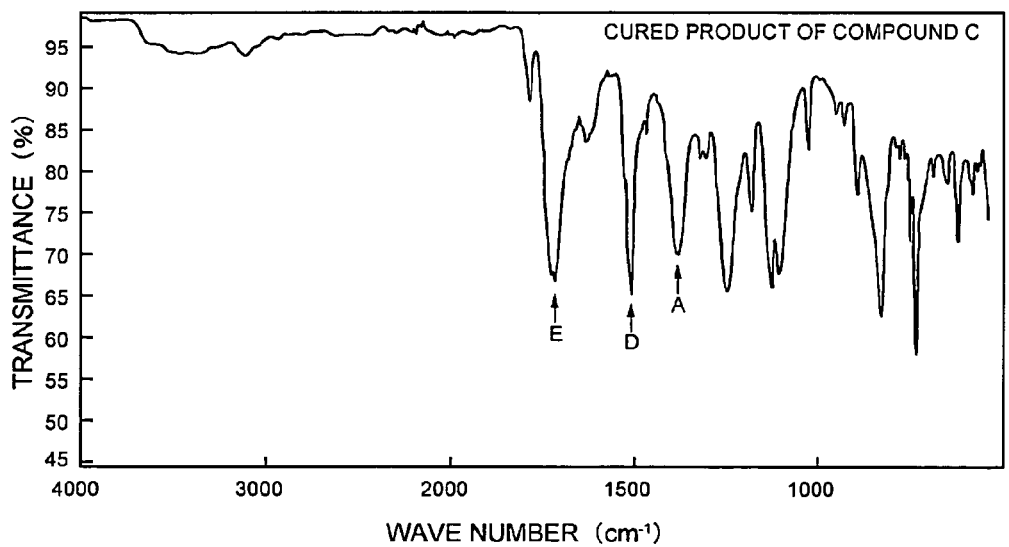
FIG. 9 is an IR spectrum chart of the thermally cured product (polyimide resin) of the compound containing an imido group (Compound C) according to the invention (Example 3)

Further, the IR spectrum chart of the compound containing an imido group obtained was illustrated in FIG. 8. The IR spectrum chart of the cured product of the compound containing an imido group (condition for thermal curing: 150° C. for 30 min), that is, the IR spectrum chart of polyimide, was illustrated in FIG. 9.

Examples 4 to 6

In the Examples 4 to 6, the solubility and the like of the compound containing an imido group were evaluated in the same manner as the Example 1 except that the average particle diameter of the compound containing an imido group (Compound A) after purification is changed to 2 μm, 5 μm, and 65 μm, respectively.

Figure 10:
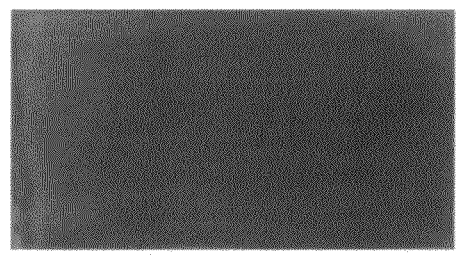
FIGS. 10A to 10C are the drawings for explaining the behavior of the polyimide film (thermally cured product) of Examples 4 to 6 of the invention.
Figure 10:
Figure 10:
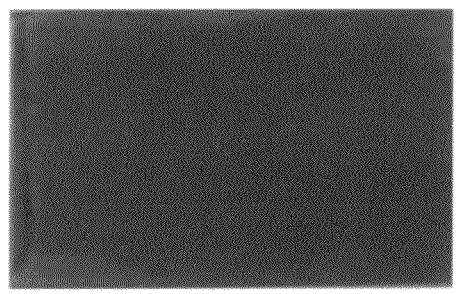

Further, in FIGS. 10A to 10C, photographic images illustrating the state of the polyimide films of the Examples 4 to 6, which are formed on a soft steel plate, are illustrated.

Comparative Example 1

In the Comparative Example 1, the solubility, low temperature curability, and adhesion property were evaluated in the same manner as the Example 1 except that sodium hydroxide is added in a molar amount of about 80 times the theoretical dissociation amount (about 66 g) to the polyimide molded article, which is then hydrolyzed under the condition including 80° C. for 7 days under atmospheric pressure and neutralized with an acidic material for full dissociation into pyromellitic acid and aromatic amines.

Comparative Example 2

In the Comparative Example 2, the solubility, low temperature curability, and adhesion property were evaluated in the same manner as the Example 1 except that potassium hydroxide is added in an amount of one molar time the theoretical dissociation amount (about 0.1 g) to the polyimide molded article, which is then hydrolyzed under the condition including 30° C. for 8 hours under atmospheric pressure and neutralized and purified with an acidic material to yield a compound which experienced almost no partial hydrolysis (Compound D).

Figure 11:
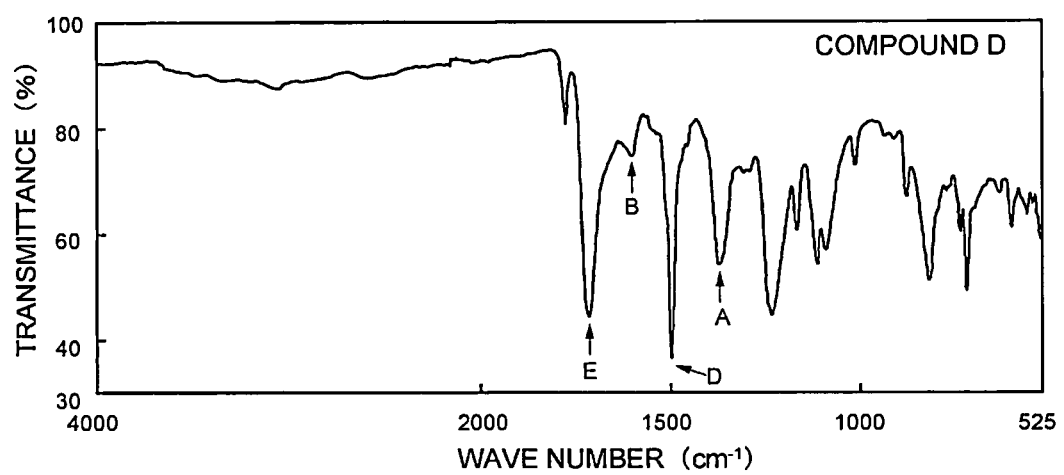
FIG. 11 is an IR spectrum chart of the compound containing an imido group (Compound D) of Comparative Example 2.

Further, the IR spectrum chart of the compound containing an imido group obtained was illustrated in FIG. 11.

TABLE 1

|  | Water (g) | Basic compound (g) | Hydrolysis temperature (° C.) | Hydrolysis time (Hrs) | Average particle diameter (μm) |
|---|---|---|---|---|---|
| Example 1 | 400 | 2 | 50 | 24 | 30 |
| Example 2 | 400 | 2 | 50 | 36 | 30 |
| Example 3 | 400 | 2 | 50 | 12 | 30 |
| Example 4 | 400 | 2 | 50 | 24 | 2 |
| Example 5 | 400 | 2 | 50 | 24 | 5 |
| Example 6 | 400 | 2 | 50 | 24 | 65 |
| Comparative Example 1 | 400 | 66 | 80 | 168 | 30 |
| Comparative Example 2 | 400 | 0.1 | 30 | 8 | 30 |

TABLE 2

|  | Imido group | Amid group | Carboxyl group | Carbonyl group | Evaluation 2 | Evaluation 3 | Evaluation 4 | Evaluation 5 |
|---|---|---|---|---|---|---|---|---|
| Example 1 | Yes | Yes | Yes | Yes | Very Good | Very Good | Very Good | Very Good |
| Example 2 | Yes | Yes | Yes | Yes | Very Good | Good | Very Good | Good |
| Example 3 | Yes | Yes | Yes | Yes | Good | Good | Good | Good |
| Example 4 | Yes | Yes | Yes | Yes | Very Good | Very Good | Very Good | Very Good |
| Example 5 | Yes | Yes | Yes | Yes | Very Good | Very Good | Very Good | Very Good |
| Example 6 | Yes | Yes | Yes | Yes | Very Good | Very Good | Very Good | Very Good |
| Comparative Example 1 | No | No | Yes | No | Very Good | Bad | Very Good | Bad |
| Comparative Example 2 | Yes | Yes | No | Yes | Bad | Bad | Bad | Very Good |

Evaluation 2: Solubility
Evaluation 3: Low temperature curability
Evaluation 4: Adhesion property
Evaluation 5: Heat resistance Example 7

Figure 12A:
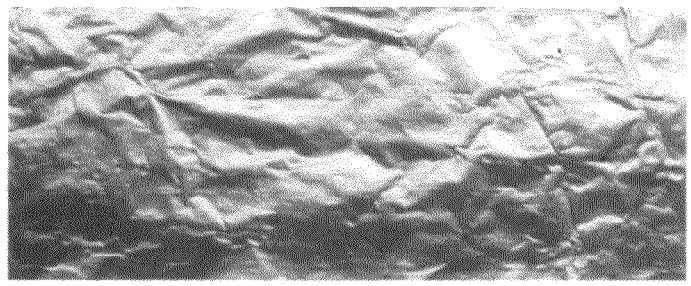
FIGS. 12A and 12B are the drawings for explaining the behavior of an aluminum foil before it is coated with the compound containing an imido group (Compound A) of Example 1 according to the invention and also an aluminum foil after it is coated with the compound and thermally cured, respectively.
Figure 12B:

In the Example 7, the compound containing an imido group (Compound A) obtained after purification in the Example 1 was coated using a bar coater on an aluminum foil illustrated in FIG. 12A followed by thermal curing for 30 min at 150° C. As a result, a composite film of polyimide with thickness of 10 μm and metal foil with thickness of 20 μm was formed as illustrated in FIG. 12B. Appearance of the film was then evaluated.

As a result, it was confirmed that, in spite of pale yellow coloration, polyimide with an excellent transparency is formed strongly on an aluminum foil.

Example 8

In the Example 8, the compound containing an imido group (Compound A) obtained after purification in the Example 1 was coated using a bar coater on a polyester film followed by thermal curing for 30 min at 150° C. As a result, a composite film of polyimide with thickness of 10 μm and polyester film with thickness of 50 μm was formed. Appearance of the film was then evaluated.

As a result, it was confirmed that, in spite of pale yellow coloration, polyimide with an excellent transparency is formed strongly on a polyester film.

Further, flame retardancy (FR) was evaluated with reference to JIS L 1091 A-1, and it was confirmed that the requirements are satisfied.

As described above, according to the invention, by partial hydrolysis of a polyimide molded article as industrial waste or the like to yield a compound containing an imido group with a specific structure which has predetermined absorption peaks in an IR spectrum chart measured by IR spectroscopic measurement, a compound containing an imido group having n excellent low temperature curability, a good solubility, and a good adhesion property, a solution of the compound containing an imido group which is obtained by dissolving the compound containing an imido group in an organic solvent, and a method for producing efficiently of the compound containing an imido group with a specific structure can be provided.

Thus, with the compound containing an imido group obtained by the invention, the obtainable polyimide showing a good heat resistance or a good adhesion property not only by thermal curing at high temperature under predetermined condition but also by thermal curing at low temperature can be provided.

Thus, it is expected that the compound containing an imido group according to the invention is preferably used for a polyimide film and a polyimide coating composition which have an excellent heat resistance or adhesion property, and also for various polyimide molded articles like a heat resistant electric part casing, a heat resistant electronic part material, a heat resistant container, a heat resistant mechanical part, and a heat resistant automotive part.

What is claimed is:

1. A compound containing an imido group, which is obtained by partial hydrolysis of a polyimide molded article, and which is capable of being thermally cured under conditions of a temperature of 200° C. or lower to yield a polyimide resin,
   wherein the compound has an absorption peak derived from an imido group at wave number of $1375\ cm^{-1}$, an absorption peak derived from an amide group at wave number of $1600\ cm^{-1}$, and an absorption peak derived from a carboxyl group at wave number of $1413\ cm^{-1}$ in the IR spectrum chart obtained by an IR spectroscopic measurement which is a FT-IR technique based on the ATR method;
   wherein, in the IR spectrum chart, when the height of absorption peak at wave number of $1500\ cm^{-1}$, which is derived from a benzene ring, is S1 and the height of absorption peak at wave number of $1375\ cm^{-1}$, which is derived from an imido group, is S2, the ratio of S1/S2 is set to be a value within the range of 3 to 10; and
   wherein the compound containing an imido group has a particulate shape and the average particle diameter of the compound containing an imido group with the particulate shape is set to be a value within the range of 0.1 to 500 μm.

2. The compound containing an imido group according to claim 1, wherein, in the IR spectrum chart, when the height of absorption peak at wave number of $1500\ cm^{-1}$, which is derived from a benzene ring, is S1 and the height of absorption peak at wave number of $1600\ cm^{-1}$, which is derived from an amide group, is S3, the ratio of S1/S3 is set to be a value within the range of 2 to 20.

3. The compound containing an imido group according to claim 1, wherein, in the IR spectrum chart, when the height of absorption peak at wave number of $1500\ cm^{-1}$, which is derived from a benzene ring, is S1 and the height of absorption peak at wave number of $1413\ cm^{-1}$, which is derived from a carboxyl group, is S4, the ratio of S1/S4 is set to be a value within the range of 8 to 30.

4. A solution of the compound according to claim 1 containing an imido group comprising a compound containing an imido group that is obtained by partial hydrolysis of a polyimide molded article and an organic solvent, wherein the compound containing an imido group has an absorption peak derived from an imido group at wave number of $1375\ cm^{-1}$, an absorption peak derived from an amide group at wave number of $1600\ cm^{-1}$, and an absorption peak derived from a carboxyl group at wave number of $1413\ cm^{-1}$ in the IR spectrum chart obtained by IR spectroscopic measurement.

5. A method for of the producing of a compound according to claim 1 containing an imido group by partial hydrolysis of a polyimide molded article, comprising the following steps (1) to (3):
   (1) chopping the polyimide molded article to prepare it with a predetermined size,
   (2) hydrolyzing the polyimide molded article with the predetermined size under the temperature condition of 50 to 100° C. in the presence of water and a basic compound to give a crude compound containing an imido group, and
   (3) purifying the crude compound containing an imido group to give a compound containing an imido group which has an absorption peak derived from an imido group at wave number of $1375\ cm^{-1}$, an absorption peak derived from an amide group at wave number of $1600\ cm^{-1}$, and an absorption peak derived from a carboxyl group at wave number of $1413\ cm^{-1}$ in the IR spectrum chart obtained by IR spectroscopic measurement.

6. The compound containing an imido group according to claim 1, wherein the compound has a weight average molecular weight within a range of 1,000 to 100,000.

7. The compound containing an imido group according to claim 1, the compound having a structure represented by the Formula (1) below:

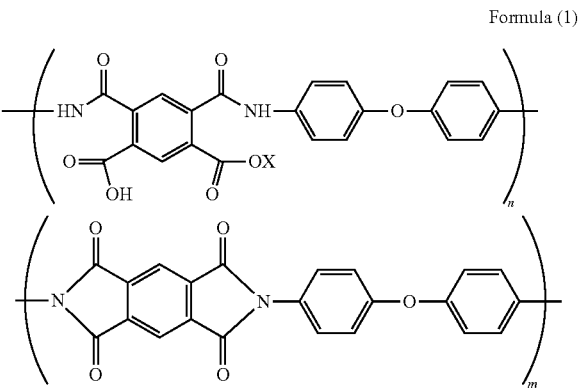

Formula (1)

-continued
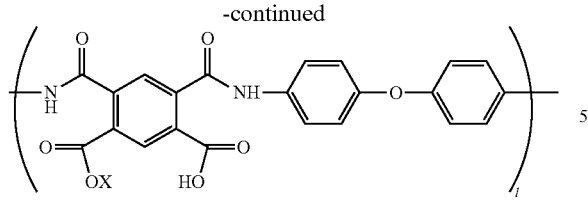
where X is an alkali metal, n and l have a value within the range of 0.1 to 0.8, and m has a value within the range of 0.2 to 0.9.
8. The compound containing an imido group according to claim 7, wherein the compound has a terminal structure of at least one of A, B and C of the Formula (2) below:

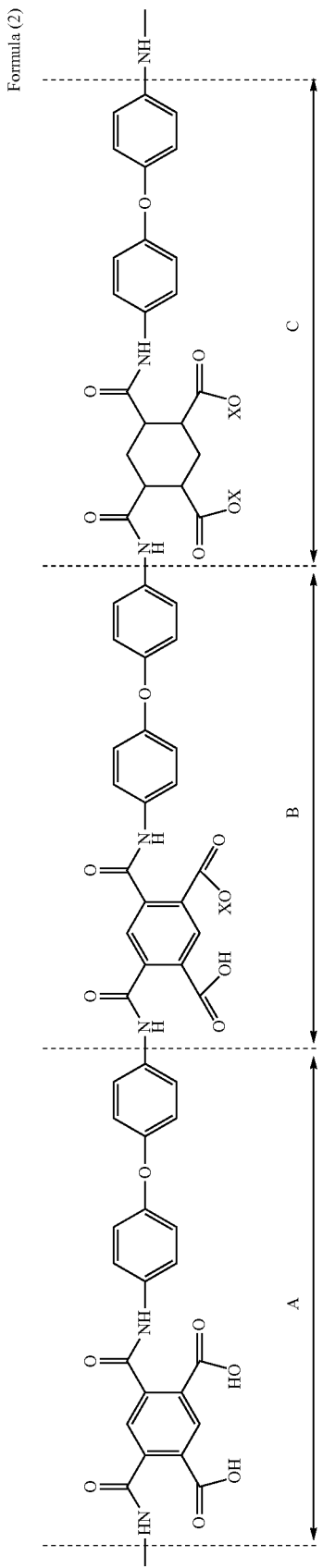

wherein X has been previously defined.

* * * * *